United States Patent [19]

Nishimura et al.

[11] Patent Number: 4,482,501
[45] Date of Patent: Nov. 13, 1984

[54] PROCESS FOR PRODUCING AMINOARYL-β-SULFATOETHYLSULFONE

[75] Inventors: Nobuzi Nishimura, Toyonaka; Utazi Sawa; Takemi Tokieda, both of Nara; Shun-ichi Hayakawa; Yasuo Tezuka, both of Ibaraki, all of Japan

[73] Assignee: Sumitomo Chemical Company, Limited, Osaka, Japan

[21] Appl. No.: 388,956

[22] Filed: Jun. 16, 1982

Related U.S. Application Data

[63] Continuation-in-part of Ser. No. 169,497, Jul. 16, 1980, Pat. No. 4,346,046.

[30] Foreign Application Priority Data

Jul. 19, 1979 [JP] Japan .................................. 54-92201
Aug. 9, 1979 [JP] Japan .................................. 54-102075
Aug. 14, 1979 [JP] Japan .................................. 54-103656
Apr. 8, 1980 [JP] Japan .................................. 55-46343

[51] Int. Cl.$^3$ ........................................... C07C 141/18
[52] U.S. Cl. ................................................. 260/458 C
[58] Field of Search .................................... 260/458 C

[56] References Cited

U.S. PATENT DOCUMENTS 4,191,703 3/1980 Steuernagel et al. ........... 260/458 C
4,315,865 2/1982 Hoyer et al. ..................... 260/458 C
4,334,076 6/1982 Steuernagel et al. ........... 260/458 C

FOREIGN PATENT DOCUMENTS 1080764 8/1967 United Kingdom .

*Primary Examiner*—Nicky Chan
*Attorney, Agent, or Firm*—Stevens, Davis, Miller & Mosher

[57] ABSTRACT

An improved process for producing sulfuric acid semi-esters of the formula:

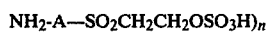

wherein A is a substituted or unsubstituted aromatic group, and n is an integer of 1 or 2, which are important as intermediates of the vinylsulfonic reactive dyes, said process comprising reacting a compound of the formula:

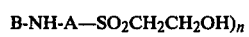

wherein A and n are as defined above, and B is hydrogen or a group capable of being hydrolyzed by an acid, with an acid.

5 Claims, No Drawings

PROCESS FOR PRODUCING AMINOARYL-β-SULFATOETHYLSULFONE

This application is a continuation-in-part application of Ser. No. 169,497, filed July 16, 1980 now U.S. Pat. No. 4,346,046.

The present invention relates to an improved process for producing sulfuric acid semiester compounds which are important as intermediates of the vinylsulfonic reactive dyes. More particularly, the invention relates to an improved process for producing a sulfuric acid semiester of the formula (I):

$$NH_2\text{-}A\text{---}SO_2CH_2CH_2OSO_3H)_n \quad (I)$$

wherein A is a substituted or unsubstituted aromatic group, and n is an integer of 1 or 2, which comprises reacting a compound of the formula (II):

$$B\text{-}NH\text{-}A\text{---}SO_2CH_2CH_2OH)_n \quad (II)$$

wherein A and n are as defined above, and B is hydrogen or a group capable of being hydrolyzed by an acid, with an acid.

The prior art methods for converting, for example, a compound of the formula (II) into a compound of formula (I) required troublesome operations and also necessitated use of a large excess of sulfuric acid for obtaining the objective compound in a high yield. More specifically, aminoaryl-B-sulfatoethylsulfone for instance has been produced by hydrolyzing acetylaminoaryl-β-hydroxyethylsulfone in hydrochloric acid or dilute sulfuric acid to obtain aminoaryl-β-hydroxyethylsulfone and then, after isolating and drying, esterifying it in concentrated sulfuric acid. According to this method, however, the isolation yield of aminoaryl-β-hydroxyethylsulfone is low and the operation is complicated since isolating and drying are required, so that this method is of little use in industrial applications.

Published Examined Japanese Patent Application No. 16617/1967 disclosed a method in which 4-acetylaminophenyl-β-hydroxyethylsulfone is hydrolyzed and simultaneously esterified by using concentrated sulfuric acid or a mixture of concentrated sulfuric acid and an organic solvent. In this method, however, as described in its Examples, in order to hydrolyze 4-acetylaminophenyl-β-hydroxyethylsulfone and convert resulting 4-aminophenyl-β-hydroxyethylsulfone and 4-aminophenyl-β-acetoxyethylsulfone into 4-aminophenyl-β-sulfatoethylsulfone, it is necessary to add a large quantity of fuming sulfuric acid in the reaction solution. For example, the amount of sulfuric acid used is as much as 8.4 to 15.6 moles per mole of the starting material, acetylaminophenyl-β-hydroxyethylsulfone. Accordingly, the product, 4-aminophenyl-β-sulfatoethylsulfone, is obtained in the form of a large volume of concentrated sulfuric acid solution or fuming sulfuric acid solution, so that it is necessary to treat a large quantity of acid no matter whether the product is put to use as is or isolated by means of dilution. Thus, this method involves the problem of increased expense due to the cost of the alkali agent required for the treatment of excess sulfuric acid and the problem of separation of the resultant sulfuric acid salt, and hence is unfit for industrial applications.

Published Examined Japanese Patent Application No. 27096/1970 shows a method of producing aminoaryl-β-sulfatoethylsulfone by hydrolyzing acetylaminoaryl-β-sulfatoethylsulfone with use of sulfuric acid having a concentration of 50% or less at 45° C. This method, however, has the drawbacks that a long time is required for the reaction and that the product yield is lowered because hydrolysis of the sulfuric ester in the β-sulfatoethylsulfonyl group takes place concurrently with hydrolysis of the acetylamino group. Moreover, even in this method which can be said to be a typical case using a relatively small amount of sulfuric acid, use of as many as 4.9 moles of sulfuric acid is required.

For The purpose of solving these problems, West German Patent Laid-Open No. 1,443,877 proposed a method of producing sulfuric acid semiester compounds in a water-soluble organic solvent such as pyridine or picoline using amidosulfonic acid in an amount of 3 to 4 moles. This method is valued in that it is capable of reducing the esterifying agent which has been used in excess in conventional methods, but this method still has the problem that the water-soluble organic solvent used must be later distilled off sufficiently under reduced pressure. Further, inspite of such distillation treatment, there still remains approximately ¼ of the used water-soluble organic solvent in the sulfuric acid semiester, so that recovery or removal of such solvent in some way or other, before the waste solution reaches the drain, is required. Another defect of this method is the fact that since it is difficult to bring a water-soluble organic solvent into a perfectly water-free state, the reaction temperature is relatively high and hence hydrolysis of amidosulfonic acid tends to take place. Thus, the hydrolyzed amidosulfonic acid must be supplemented, resulting in use of a considerable amount of excess esterifying agent.

As a result of extensive studies for eliminating said disadvantages of the heretofore known methods, the present inventors have succeeded in obtaining an improved process for producing a high-purity sulfuric acid semiester compound in a substantially quantitative yield and in an industrially advantageous way by using a substantially theoretical amount of an acid and without producing any waste solution which might cause environmental. This process comprises reacting a compound of said formula (II) with an acid in a specific pattern of reaction.

Thus, the present invention provides a process for producing a sulfuric acid semiester of the formula (I):

$$NH_2\text{-}A\text{---}SO_2CH_2CH_2OSO_3H)_n \quad (I)$$

wherein A is phenylene or naphthylene, which may be substituted with one or two methyl or methoxy groups, and n is an integer of 1 or 2, which comprises subjecting a mixture of an acid and a compound of the formula (II), $$B\text{-}NH\text{-}A\text{---}SO_2CH_2CH_2OH)_n \quad (II)$$

wherein A and n are as defined above, and B is hydrogen or a group capable of being hydrolyzed by an acid, to reaction, while removing a volatile matter from the reaction system, in a reaction zone capable of kneading the mixture, whereby esterification of said compound of the formula (II) wherein B is hydrogen or hydrolysis and esterification of said compound of the formula (II) wherein B is a group capable of being hydrolyzed by an acid is effected, the acid in the reaction system being sulfuric acid, the amount of the acid being 1 to 2 moles per mole of β-hydroxyethylsulfonyl group in the compound of the formula (II), and the initial concentration of the acid being 40 to 98% by weight.

The present invention is described in further detail hereinbelow.

The compounds of formula (II) include but are not limited to the following:

4-(amino or acetylamino)phenyl-β-hydroxyethylsulfone,
2-methoxy-5-(amino or acetylamino)phenyl-β-hydroxyethylsulfone,
2-methyl-4-(amino or acetylamino)-5-methoxyphenyl-β-hydroxyethylsulfone,
3-(amino or acetylamino)-4-methoxyphenyl-β-hydroxyethylsulfone,
3-(amino or acetylamino)phenyl-β-hydroxyethylsulfone,
4-(amino or acetylamino)-2,5-dimethoxyphenyl-β-hydroxyethylsulfone,
5-(amino or acetylamino)-2,4-dimethoxyphenyl-β-hydroxyethylsulfone,
2-methyl-5-(amino or acetylamino)phenyl-β-hydroxyethylsulfone,
2-(amino or acetylamino)phenyl-β-hydroxyethylsulfone,
5-(amino or acetylamino)-1-naphthyl-β-hydroxyethylsulfone,
4-(amino or acetylamino)-1-naphthyl-β-hydroxyethylsulfone,
5-(amino or acetylamino)-2-naphthyl-β-hydroxyethylsulfone, and
7-(amino or acetylamino)-1-naphthyl-β-hydroxyethylsulfone.

These compounds can be used even in a hydrous state. This makes it possible to avoid troublesome operations such as drying and pulverization, thereby making the method of the present invention more advantageous than the conventional methods.

The acids usable in the present invention include sulfuric acid, sulfamic acid, chlorosulfonic acid and mixtures of sulfuric acid with sulfamic acid, chlorosulfonic acid or sulfur trioxide. Among these acids, sulfuric acid is most preferred from the industrial view point. In some cases where a certain specified type of compound is used as a starting material, a mixture of sulfuric acid and sulfamic acid allows advantageous advancement of the reaction and proves desirable in respect of the material of the reaction apparatus.

The amount of the acid used in this invention is within the range of 1 to 2 moles per mole of β-hydroxyethylsulfonyl group in the compound of the formula (II).

The initial concentration of sulfuric acid in the reaction system

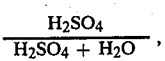

although not limited to any specific range, is usually 20 to 100 wt%, preferably 40 to 98 wt% and more preferably 40 to 78 wt%. If the compound of the formula (II) is in a hydrous state, the concentration of sulfuric acid used is properly selected according to the degree of the hydrous state, and in some cases, fuming sulfuric acid is used.

The reaction temperature is suitable decided depending on the properties of the starting compound, the pattern of reaction and the reaction apparatus employed, but usually it is between 40° C. and 250° C., preferably 50° to 180° C., more preferably 50° to 140° C. The higher the temperature, the more facilitated is the progress of the reaction, but too high a temperature tends to cause a side reaction thereby adversely affecting the objective product. If an apparatus capable of shortening the reaction time is employed, a relatively high temperature can be used.

Organic solvents that are inert to said acids and have the ability to form an azeotrope with water or water and volatile matter at 50°–200° C. may be used. Examples of such organic solvents include cyclohexane, heptane, benzene, toluene, xylene, solvent naphtha, trichloroethane, dichloropropane, trichloroethylene, tetrachloroethane, perchloroethylene, chlorobenzene, dichlorobenzene, nitrobenzene and methyl isobutyl ketone. Such organic solvents are used in an amount of 0.1 to 10 times, preferably 0.1 to 8 times the weight of the starting compound of the formula (II).

In carrying out the reaction by means of kneading, there is preferably employed an apparatus that has a batchwise or continuous stirring or grinding capacity such as the apparatus generally used for mixing viscous or tacky materials. Examples of the batchwise apparatus usable in this the present invention are ribbon mixers, pug mills and double-arm kneaders (for example, dispersion kneader); and examples of the continuous apparatus are continuous kneaders and auger extruders.

In the present invention, the volatile matter to be removed from the reaction system is variable depending on the type of starting compound (II) and acid used, and includes water and other by-produced matters such as acetic acid, hydrogen chloride, ammonia, carbon dioxide gas, etc. For facilitating the removal of volatile matter, an inert gas such as nitrogen gas, air or carbon dioxide gas may be blown into the reaction solution or the operation may be performed undder reduced pressure; and in order to improve heat transfer, an inert material such as diatomaceous earth, activated clay, active carbon, silica gel, brown coal, etc., may be used. The reaction mixture comprising the desired sulfuric acid semiester obtained according to the process of the present invention itself or a dilute solution obtainable by pouring the reaction mixture into water and then neutralizing with an alkali agent such as sodium hydroxide, sodium carbonate, sodium hydrogen carbonate or potassium carbonate etc., may be immediately used as an intermediate for reactive dyes. The reaction mixture obtained according to the process of the present invention using an organic solvent and/or inert material such as diatomaceous earth, activated clay, etc., is poured into water and then neutralized with an alkali agent as described above. After the organic solvent and/or the inert material are removed by filtration, decantation or the like, the obtained dilute solution of the alkali metal salt of the sulfuric acid semiester in water may be used as an intermediate for reactive dyes.

The process of the present invention will now be described in further detail by way of the following examples, but the invention is not limited to these examples. All "parts" and "%" in the following examples are by weight unless otherwise specified.

EXAMPLE 1

266.5 Parts of 7-amino-1-naphthyl-β-hydroxyethylsulfone (purity: 95%), 120 parts of 98% sulfuric acid (molar ratio: 1.2) and 133 parts of o-dichlorobenzene were fed into a double-arm kneader (manufactured by Moriyama Seisakujo Co.) operated at 80/60 r.p.m. and the mixture was maintained at 100°–105° C. under reduced pressure (150 mmHg) for 5 hours while distilling off produced water to complete the reaction. The obtained reaction product was analyzed by a liquid chromatography, obtaining 7-amino-1-naphthyl-β-sulfatoethylsulfone in a yield of 93%.

EXAMPLE 2

247.5 Parts of 4-acetylaminophenyl-β-hydroxyethylsulfone (purity: 98.2%) and 105 parts of 98% sulfuric acid (1.05 times in molar quantity) were fed into a commercial two-shaft double-arm kneader (Inoue Seisakujo Co.) having a heating or cooling jacket and operated at 60/45 r.p.m., and the mixture was maintained at 100°–105° C. under reduced pressure (400 mmHg) for 6 hours while distilling off water and acetic acid. A liquid chromatograph of the reaction product showed 96% yield of 4-aminophenyl-β-sulfatoethylsulfone. It was also found that there were contained small quantities of 4-aminophenyl-β-hydroxyethylsulfone and 4-aminophenyl-β-acetoxyethylsulfone.

EXAMPLE 3

281.6 Parts of 2-methoxy-5-acetylaminophenyl-β-hydroxyethylsulfone (purity: 97%) were added in 165.8 parts of 65% sulfuric acid (1.1 times in molar quantity) under stirring, and the mixture was maintained at 100°–105° C. for 2 hours. Then this mixture was poured into a ribbon mixer (manufactured by Moriyama Seisakujo Co.) operated at 70 r.p.m. and having already contained therein 500 parts of diatomaceous earth, said pouring being effected for a period of 20 minutes. The mixture was maintained at 120°–125°° C. for 7 hours while distilling off acetic acid and water. A liquid chromatograph of the reaction product showed 94% yield of 2-methoxy-5-aminophenyl-β-sulfatoethylsulfone.

EXAMPLE 4

281.5 Parts of 3-acetylamino-4-methoxyphenyl- β-hydroxyethylsulfone (purity: 97%) and 134.1 parts of 95% sulfuric acid (1.3 times in molar quantity) were supplied into a pug mill (Kurimoto Iron Works) operated at 80 r.p.m., and the mixture was maintained at 100°–105° C. under reduced pressure (500 mmHg) for 4 hours while distilling off water and acetic acid. Analysis of the reaction mixture by a liquid chromatography showed a 94% yield of 3-amino-4-methoxyphenyl-β-sulfatoethylsulfone.

EXAMPLE 5

247.5 Parts of 4-acetylaminophenyl-β-hydroxyethylsulfone (purity: 98.2%) and 300 parts of diatomaceous earth were fed into a two-shaft double-arm kneader (Inoue Seisakujo Co.) operated at 60/45 r.p.m., followed by the pouring thereinto of 105 parts of 98% sulfuric acid (molar ratio: 1.05). Then 250 parts of xylene were added dropwise under reduced pressure (500 mmHg), and the mixture was maintained at 120°–125° C. for 6 hours while distilling off acetic acid and water to complete the reaction. A liquid chromatograph of the reaction product showed production of 4-amino-β-sulfatoethylsulfone in a yield of 95%.

EXAMPLE 6.

304.5 Parts of 3-aminophenyl-β-hydroxyethylsulfone (purity: 66%) were fed, in the form of a wet cake, into a two-shaft double-arm kneader (Inoue Seisakujo Co.) having a heating-cooling jacket and operated at 60/45 r.p.m., and water was distilled off under reduced pressure (600 mmHg) at 100°–105° C. At a point when distilling-off of water was no longer noticed, pressure reduction was released and the mixture was cooled to 50° C., 120 parts of 65% fuming sulfuric acid (molar ratio: 1.4) were added and the mixture was maintained at 50°–60° C. for 3 hours. Production of 3-aminophenyl-β-sulfatoethylsulfone in a yield of 92% was ascertained as a result of liquid chromatographic analysis of the reaction product.

EXAMPLES 7–11

The reaction process of Example 2 was repeated but by changing the starting material, type of reactor, its operating speed, sulfuric acid concentration, amount of sulfuric acid added and degree of pressure reduction as shown in Table 1. The objective products were obtained in the yields also shown in Table 1.

TABLE 1

| Example No. | Starting material | Reactor | Operating speed rpm | Sulfuric acid concentration (%) | Amount of sulfuric acid (molar ratio) | Pressure (mmHg) | Reaction temperature (°C.) | Yield (%) |
|---|---|---|---|---|---|---|---|---|
| 7 | 4-Amino-1-naphthyl-β-hydroxyethylsulfone | Two-shaft double arm kneader | 60/45 | 90 | 1.2 | Normal pressure | 115–120 | 93 |
| 8 | 2-Methyl-4-acetylamino-5-methoxy-phenyl-β-hydroxyethylsulfone | Dispersion kneader | 70 | 70 | 1.5 | 100 | 80–85 | 94 |
| 9 | 3-Aminophenyl-β-hydroxyethylsulfone | Double-arm kneader | 80/60 | 98 | 1.05 | Normal pressure | 130–135 | 96 |
| 10 | 7-Amino-1-naphthyl-β-hydroxyethylsulfone | Two shaft double-arm kneader | 60/40 | 98 | 1.2 | 500 | 95 | 94 |
| 11 | 4-Acetylaminophenyl-β-hydroxyethyl- | Kurimoto cosntinuous | 20 | 70 | 1.05 | Normal pressure | 120–125 | 94 |

TABLE 1-continued

| Example No. | Starting material | Reactor | Operating speed rpm | Sulfuric acid concentration (%) | Amount of sulfuric acid (molar ratio) | Pressure (mmHg) | Reaction temperature (°C.) | Yield (%) |
| --- | --- | --- | --- | --- | --- | --- | --- | --- |
| | sulfone | kneader | | | | | | |

EXAMPLE 12

304.5 Parts of 3-aminophenyl-$\beta$-hydroxyethylsulfone (purity: 66%), in the form of a wet cake, were fed into a two-shaft double-arm kneader (Inoue Seisakujo Co.) having a heating-cooling jacket and operated at 60/45 r.p.m. and water was distilled off under reduced² pressure (600 mmHg) at 100°–105° C. The mixture was further added with 135.8 parts of sulfamic acid (molar ratio: 1.4) and maintained at 90°–95° C. for 6 hours. By-produced ammonia was removed as ammonium salt during this period. Liquid chromatographic analysis of the resulting reaction product showed 95% yield of 3-aminophenyl-$\beta$-sulfatoethylsulfone.

EXAMPLE 13

247.5 Parts of 4-acetylaminophenyl-$\beta$-hydroxyethylsulfone (purity: 98.2%) and 205.8 parts of 50% sulfuric acid were fed into a two-shaft double-arm kneader (manufactured by Inoue Seisakusho) operated at 60 r.p.m., and the mixture was maintained at 100° to 105° C. under reduced pressure (400 mmHg) for 10 hours while distilling off the produced water and acetic acid. The reaction product was analyzed by liquid chromatography, obtaining 4-aminophenyl-$\beta$-sulfatoethylsulfone in a 96% yield, and 4-aminophenyl-$\beta$-hydroxyethylsulfone and 4-aminophenyl-$\beta$-acetoxyethylsulfone in small amounts.

EXAMPLE 14

281.6 parts of 2-methoxy-5-acetylaminophenyl-$\beta$-hydroxyethylsulfone (purity: 97%) were added into 165.8 parts (molar ratio: 1.1) of 65% sulfuric acid while being stirred, and the mixture was maintained at 100° to 105° C. for 2 hours. The mixture was fed within 20 minutes into a ribbon mixer operated at 70 r.p.m. into which 500 parts of diatomaceous earth had been fed. The mixture was kept at 120° to 125° C. for 7 hours, during which the produced acetic acid and water were distilled off. The reaction product was analyzed by liquid chromatography, obtaining 2-methoxy-5-aminophenyl-$\beta$-sulfatoethylsulfone in 94% yield.

EXAMPLE 15

281.5 Parts of 3-acetylamino-4-methoxyphenyl-$\beta$-hydroxyethylsulfone (purity: 97%) and 196 parts of 65% sulfuric acid (molar ratio: 1.3) were fed into a pug-mill (manufactured by Kurimoto Iron Works) operated at 80 r.p.m., and the mixture was maintained at 100° to 105° C. under reduced pressure (400 mmHg) for 6 hours, while distilling off the produced water and acetic acid. The reaction product was analyzed by liquid chromatography, obtaining 3-amino-4-methoxyphenyl-$\beta$-sulfatoethylsulfone in a 94% yield.

EXAMPLE 16

292.9 Parts of 2-methyl-4-acetylamino-5-methoxyphenyl-$\beta$-hydroxyethylsulfone (purity: 98%) and 500 parts of diatomaceous earth were fed into a dispersion kneader (manufactured by Inoue Seisakusho) operated at 70 r.p.m. and then 210 parts of 70% sulfuric acid (molar ratio: 1.5) were added thereto. The mixture was maintained at 95° to 100° C. under reduced pressure (300 mmHg) for 7 hours while distilling off the produced water and acetic acid. The reaction product was analyzed by liquid chromatography, obtaining 2-methyl-4-amino-5-methoxyphenyl-$\beta$-hydroxyethylsulfone in a 94% yield.

EXAMPLE 17

209.4 Parts of 3-aminophenyl-$\beta$-hydroxyethyl-sulfone (purity: 96%) and 147 parts (molar ratio: 1.05) of 70% sulfuric acid were fed into a double arm kneader (manufactured by Inoue Seisakusho) operated at 80 r.p.m. and the mixture was maintained at 130° to 135° C. for 5 hours, while distilling off the produced water. The reaction product was analyzed by liquid chromatography, obtaining 3-aminophenyl-$\beta$-sulfatoethylsulfone in a 95% yield.

EXAMPLE 18

266.5 Parts of 7-amino-naphthyl-$\beta$-hydroxyethylsulfone (purity: 95%), 156.8 parts (molar ratio: 1.2) of 75% sulfuric acid and 500 parts of diatomaceous earth were fed into a two-shaft double arm kneader (manufactured by Inoue Seisakusho) operated at 60 r.p.m. and the mixture was maintained at 90° to 95° C. for 8 hours, while distilling off the produced water. The reaction mixture was analyzed by liquid chromatography, obtaining 7-amino-1-naphthyl-$\beta$-sulfatoethylsulfone in a 94% yield.

EXAMPLES 19 to 21

Example 18 was repeated, except that the reaction was carried out under the conditions as described in the following table.

| Example No. | Starting material | Sulfuric acid Concentration (%) | Amount | Pressure (mmHg) | Temperature (°C.) | Yield (%) |
| --- | --- | --- | --- | --- | --- | --- |
| 19 | 4-Amino-2,5-dimethoxy-phenyl-$\beta$-hydroxyethyl sulfone | 60 | 1.7 | 200 | 90–95 | 93 |
| 20 | 3-Chloro-4-aminophenyl-$\beta$-hydroxyethyl-sulfone | 45 | 1.1 | Atmospheric pressure | 120–125 | 94 |
| 21 | 4-Amino-1-naphthyl- | 70 | 1.2 | Atmospheric | 115–120 | 93 |

| Example No. | Starting material | Sulfuric acid Concentration (%) | Amount | Pressure (mmHg) | Temperature (°C.) | Yield (%) |
|---|---|---|---|---|---|---|
| | β-hydroxyethyl-sulfone | | | pressure | | |

EXAMPLE 22

361 parts of 3-acetylamino-4-methoxyphenyl-β-hydroxyethylsulfone (wet cake, purity: 75.6%) were added to 116.5 parts (molar ratio: 1.2) of 5% oleum under external cooling, while being stirred, and then kept at 100° to 105° C. for 2 hours. The resulting mixture was fed into a two-shaft double arm kneader (manufactured by Inoue Seisakusho) operated at 60 r.p.m., in which 500 parts of diatomaceous earth had been placed. The mixture was maintained at 100° to 105° C. under reduced pressure (500 mmHg) for 7 hours, while distilling off the produced water and acetic acid. 3-Amino-4-methoxyphenyl-β-sulfatoethylsulfone was obtained in a 93% yield.

EXAMPLE 23

2475 Parts of 4-acetylaminophenyl-β-hydroxy ethylsulfone (purity: 98.2%) were added to 1470 parts (molar ratio 1.05) of 70% sulfuric acid under stirring. The mixture was maintained at 100° to 105° C. for 1 hour and then continuously fed into a Kurimoto continuous kneader at a rate of 5 parts per minute, while distilling off the produced water and acetic acid. The powdery reaction product obtained continuously was analyzed by paper-chromatography, obtaining 4-aminophenyl-β-sulfatoethylsulfone in a 94% yield, and 4-aminophenyl-β-hydroxyethylsulfone and 4-aminophenyl-β-acetoxyethylsulfone in small amounts.

REFERENTIAL EXAMPLE 1

The reaction mixture obtained in Example 2 was put into icy water and, without isolating the product, diazotized in a normal way with hydrochloric acid and sodium nitrite, followed by coupling with 38.9 parts of 1amino-8-naphthol-3,6-disulfonic acid (purity: 80%) in a normal manner and spray drying of the obtained solution. There was obtained a black dye known as Reactive Black 5 in Color Index, said black dye being low in inorganic salt content and high in concentration.

REFERENTIAL EXAMPLE 2

The reaction product obtained in Example 5 was put into icy water and, after neutralization with sodium carbonate and successive removal of xylene and diatomaceous earth, the product was diazotized in a known way with hydrochloric acid and sodium nitrite. This was followed by coupling in a usual way with 1.1 time the molar quantity of 3-sulfo-7-acetylamino-naphthol and the whole product was spray-dried, whereby there was obtained an orange dye known as C.I. Reactive Orange 16 in a high yield. The solution formed by adding 4.0 parts of diethylene glycol monobutyl ether to the reaction solution before spray-drying was a concentrated aqueous solution which was low in sodium sulfate content, caused no crystal precipitation even if left at low temperature and had excellent storage stability.

When cellulose fibers were dyed in a common way by using these dye products, there were obtained the fast and concentrated reddish orange dyed fabrics.

What is claimed is:

1. A process for producing a sulfuric acid semiester of the formula (I):

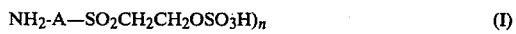

$$NH_2-A-SO_2CH_2CH_2OSO_3H)_n \qquad (I)$$

wherein A is phenylene or naphthylene, which may be substituted with one or two methyl or methoxyl groups, and n is an integer of 1 or 2, which comprises subjecting a mixture of an acid and a compound of the formula (II),

$$B-NH-A-SO_2CH_2CH_2OH)_n \qquad (II)$$

wherein A and n are as defined above, and B is hydrogen or a group capable of being hydrolyzed by an acid, to reaction, while removing a volatile matter from the reaction system and subjecting the mixture to a kneading action, whereby esterification of said compound of the formula (II) wherein B is hydrogen or hydrolysis and esterification of said compound of the formula (II) wherein B is a group capable of being hydrolyzed by an acid is effected, the acid in the reaction system being sulfuric acid, the amount of the acid being 1 to 2 moles per mole of β-hydroxyethylsulfonyl group in the compound of the formula (II), and the initial concentration of the acid being 40 to 98% by weight.

2. The process according to claim 1, wherein the reaction is carried out at a temperature of 40° to 250° C.

3. The process according to claim 1, wherein the initial concentration of the acid is 40 to 78% by weight.

4. The process according to claim 1, wherein the reaction is carried out in the presence of diatomaceous earth, activated clay, active carbon, silica gel or brown coal.

5. The process according to claim 1, wherein the reaction is carried out in the presence of an inert gas or under a reduced pressure.

* * * * *